United States Patent
Lukacs

(10) Patent No.: US 7,914,614 B1
(45) Date of Patent: Mar. 29, 2011

(54) HERBAL PAINT

(76) Inventor: Maria Lukacs, St. Petersburg, FL (US)

( * ) Notice: Subject to any disclaimer, the term of this patent is extended or adjusted under 35 U.S.C. 154(b) by 465 days.

(21) Appl. No.: 12/082,918

(22) Filed: Apr. 15, 2008

(51) Int. Cl.
- *C09D 5/14* (2006.01)
- *A01N 65/00* (2009.01)
- *A01N 65/06* (2009.01)
- *A01N 65/22* (2009.01)
- *A01N 65/24* (2009.01)
- *A01N 65/36* (2009.01)

(52) U.S. Cl. .......... 106/18; 106/217.7; 106/287.35; 424/725; 424/736; 424/742; 424/769; 424/774; 424/778

(58) Field of Classification Search .......... 106/162.1, 106/217.7, 243, 287.26, 287.35, 18; 424/725, 424/736, 742, 769, 774, 778
See application file for complete search history.

(56) References Cited

U.S. PATENT DOCUMENTS

| | | | | |
|---|---|---|---|---|
| 3,663,253 A * | 5/1972 | Stone | | 106/15.05 |
| 5,397,385 A * | 3/1995 | Watts | | 106/18.32 |
| 5,843,215 A * | 12/1998 | Whalon et al. | | 106/18.29 |
| 5,985,010 A * | 11/1999 | Etscorn et al. | | 106/2 |
| 6,505,436 B2 | 1/2003 | Neumann | | |
| 6,632,839 B2 | 10/2003 | Neumann | | |
| 6,730,332 B2 | 5/2004 | Agarwal et al. | | |
| 7,333,795 B2 * | 2/2008 | Dorsey et al. | | 455/404.1 |
| 7,514,102 B1 * | 4/2009 | Overman | | 424/724 |
| 2005/0244515 A1 * | 11/2005 | Tsuchida et al. | | 424/725 |
| 2006/0024344 A1 * | 2/2006 | Matos et al. | | 424/405 |
| 2006/0034898 A1 * | 2/2006 | Amodt et al. | | 424/443 |
| 2006/0057172 A1 * | 3/2006 | Anderson et al. | | 424/405 |
| 2006/0177472 A1 * | 8/2006 | Tomioka | | 424/405 |
| 2007/0020344 A1 * | 1/2007 | Bohlin et al. | | 424/725 |
| 2007/0071778 A1 * | 3/2007 | Narayanan et al. | | 424/400 |
| 2008/0038373 A1 * | 2/2008 | Belbachir et al. | | 424/664 |
| 2009/0130236 A1 * | 5/2009 | Tsuchida et al. | | 424/725 |

OTHER PUBLICATIONS

Paints, © 2005 Bruce MacEvoy (Aug. 2005).*

* cited by examiner

*Primary Examiner* — David M Brunsman
(74) *Attorney, Agent, or Firm* — Edward P Dutkiewicz

(57) ABSTRACT

A herbal paint mixture comprising, in combination, a carrier paint having a first volume and an herbal mixture having a second volume. The first volume and the second volume being mixed together.

18 Claims, No Drawings

HERBAL PAINT

NEW RULE 1.78(F)(1) DISCLOSURE

The Applicant has not submitted a related pending or patented non-provisional application within two months of the filing date of this present application. The invention is made by a single inventor, so there are no other inventors to be disclosed. This application is not under assignment to any other person or entity at this time.

BACKGROUND OF THE INVENTION

1. Field of the Invention

The present invention relates to a herbal paint and more particularly pertains to wa way of integrating herbal components into a paint.

2. Description of the Prior Art

The use of herbal therapy is known in the prior art. More specifically, herbal therapy previously devised and utilized for the purpose of preventing and treating physical conditions are known to consist basically of familiar, expected, and obvious components, notwithstanding the myriad of formulations encompassed by the crowded prior art which has been developed for the fulfillment of countless objectives and requirements.

While the prior art devices fulfill their respective, particular objectives and requirements, the aforementioned patents do not describe herbal paint that allows the user to apply an herbal therapy as part of a paint.

In this respect, the herbal paint according to the present invention substantially departs from the conventional concepts and formulations of the prior art, and in doing so provides a formulation primarily developed for the purpose of providing the user with a way of integrating herbal components into a paint.

Therefore, it can be appreciated that there exists a continuing need for a new and improved herbal paint which can be used for integrating herbal components into a paint. In this regard, the present invention substantially fulfills this need.

SUMMARY OF THE INVENTION

In view of the foregoing disadvantages and shortcomings inherent in the known types of herbal therapy now present in the prior art, the present invention provides an improved herbal paint. As such, the general purpose of the present invention, which will be described subsequently in greater detail, is to provide a new and improved herbal paint which has all the advantages of the prior art and none of the disadvantages.

To attain this, the present invention essentially comprises an herbal paint mixture comprising several components, in combination. The herbal paint mixture is made up of a carrier paint and an herbal additive. In the preferred embodiment the carrier paint has a color added thereto. In other embodiments, the carrier paint may be a clear paint, either oil based or water based. The carrier paint has a consistency for allowing the paint to be applied to and adherent to a surface. The surface referred to may be a wall, ceiling, floor, or any surface of a room. The mixture of herbs is determined by the room being painted and the effect desired. Like medications, specific herbs have specific pharmacologic properties. Herbal oils are used, but one may place ground up herbs, or water soluable extracts within the carrier paint. The herbal oils are mixed with the carrier paint and then the paint is applied to a surface to be treated with the herbal paint. The surface may be an interior wall or ceiling of a play room, a workout area, or a bedroom, to name a few. The correlation between the herbal oils selected and the rooms to be treated is a matter of choice.

The oils are mixed with a mixture of natural honey, milk fat, alcohol and olive oil.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of the formulation of, and the arrangements of, the components set forth in the following description. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the other formulations, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved herbal paint which has all of the advantages of the prior art herbal therapy and none of the disadvantages.

It is another object of the present invention to provide a new and improved herbal paint which may be easily and efficiently manufactured and marketed.

It is further object of the present invention to provide a new and improved herbal paint which is of durable and reliable constructions.

An even further object of the present invention is to provide a new and improved herbal paint which is susceptible of a low cost of manufacture with regard to both materials and labor, and which accordingly is then susceptible of low prices of sale to the consuming public, thereby making such herbal paint economically available to the buying public.

Even still another object of the present invention is to provide a herbal paint for wa way of integrating herbal components into a paint.

Lastly, it is an object of the present invention to provide a new and improved herbal paint mixture comprising, in combination, a carrier paint having a first volume and an herbal mixture having a second volume. The first volume and the second volume being mixed together.

These together with other objects of the invention, along with the various features of novelty which characterize the invention, are pointed out with particularity in the claims annexed to and forming a part of this disclosure. For a better understanding of the invention, its advantages and the specific objects attained by its uses, reference should be had to the accompanying descriptive matter concerning the preferred embodiments of the invention.

DESCRIPTION OF THE PREFERRED EMBODIMENT

The preferred embodiment of the new and improved herbal paint embodying the principles and concepts of the present invention will be described.

The present invention, the herbal paint 10 is comprised of a plurality of components. Such components in their broadest context include a carrier paint, a mixture of herbal oils, and a mixture of natural liquids, such as honey and ethyl alcohol.

Such components are combined so as to attain the desired objective.

The herbal paint mixture comprises several components, in combination. The herbal paint mixture is made up of a carrier paint and an herbal additive. In the preferred embodiment the carrier paint has a color added thereto. In other embodiments, the carrier paint may be a clear paint, either oil based or water based. The carrier paint has a consistency for allowing the paint to be applied to and adherent to a surface. The surface referred to may be a wall, ceiling, floor, or any surface of a room. A single herbal oil or a mixture of herbal oils may be used. Ground herbs may also be used in place of the herbal oil, or ground herbs and an herbal oil may be used together. The selections of the herbs or herbal oil to be used is determined by the room being painted and the effect desired. Like medications, specific herbs have specific pharmacologic properties, and the use of specific herbs has specific beneficial objectives.

The herbal oils selected have boiling points that are higher than are encountered in normal temperatures within an application, and therefore will not vaporize. The boiling temperatures for such oil based additives are each over one hundred degrees centigrade, thereby preventing evaporation before and during application and drying.

The preparation of a herbal paint mixture for painting a fitness, or workout, comprises using a first volume of a carrier paint. A second volume of an herbal mixture is then mixed into the carrier paint. The second volume comprises between about 2 and 8 drops of *Citrus Medica* Var. *Limonum*. To this is added between about 5 and 15 drops of *Cynnamomum ceylonicum*, and between about 5 and 15 drops of *Pogostemon patchouli*. Further added into the second volume is between about 5 and 15 drops of *Rosmarinus officinalis*, between about 5 and 15 drops of *Eugenia coryophyllata*, and between about 2 and 8 drops of *Pimpinella anisum*. The above composes an herbal oil component of the second volume. The second volume also has added into it between about 2 and 8 tablespoons of olive oil, between about 1 and 8 tablespoons of an alcohol, the preferred embodiment utilizing ethyl alcohol, between about ½ and 3 tablespoons of natural honey, and between about 1 and 5 deciliters of milk Fat.

The use of the natural liquids, such as honey, ethyl alcohol olive oil and milk fat enhances the effect and duration of the herbal oils. In some applications the natural liquids may be eliminated from the mixture, and the mixture may be made with the carrier paint and one or more herbal oils or herbs.

The preparation of a herbal paint mixture for painting a child's room, is the use of a first volume of a carrier paint. A second volume of an herbal mixture is then mixed into the first volume of the carrier paint. The second volume comprises between about 10 and 20 drops of *Citrus sinensis*, between about 10 and 20 drops of *Citrus nobilis*, between about 2 and 8 drops of *Lavandula officinalis*, and between about 2 and 8 drops of *Pinus sylvestris*. To the second volume also has added into it between about 2 and 8 tablespoons of Olive Oil, between about 1 and 8 tablespoons of an alcohol, the preferred embodiment utilizing ethyl alcohol, between about ½ and 3 tablespoons of natural honey, and between about 1 and 5 deciliters of milk Fat.

The preparation of a herbal paint mixture for painting a bed room, is the use of a first volume of a carrier paint. A second volume of an herbal mixture is then mixed into the carrier paint. The second volume comprises between about 5 and 15 drops of *Aniba roseadora*, between about 5 and 15 drops of *Levendula off*, between about 5 and 15 drops of *Citrus medica* var. *limonum*, between about 3 and 12 drops of *Camnphora officinarum*, between about 2 and 6 drops of *Citrus sinensis*, and between about 4 and 12 drops of *Oscimum basilicum*. The second volume also has added into it between about 2 and 8 tablespoons of olive oil, between about 1 and 8 tablespoons of an alcohol, the preferred embodiment utilizing ethyl alcohol, between about ½ and 3 tablespoons of natural honey, and between about 1 and 5 deciliters of milk fat.

The preparation of a herbal paint mixture for painting a work room, is the use of a first volume of a carrier paint. A second volume of an herbal mixture is then mixed into the first volume of carrier paint. The second volume comprises between about 5 and 15 drops of *Citrus sinesis*, between about 10 and 20 drops of *Thymus vulgaris*, between about 2 and 8 drops of *Eucalyptus globules*, between about 2 and 8 drops of *Oscimum basilicum*, between about 10 and 20 drops of *Citrus aurantium*, and between about 5 and 15 drops of *Pinus sylvestris*. The second volume also has added into it between about 2 and 8 tablespoons of olive oil, between about 1 and 8 tablespoons of an alcohol, the preferred embodiment utilizing ethyl alcohol, between about ½ and 3 tablespoons of natural honey, and between about 1 and 5 deciliters of milk fat. The paint mixture being formulated for application to the surface in a work room.

The use of herbal compounds in a paint carrier is also effective to treat room with the presence of mildew. The preparation of a herbal paint mixture for painting a room with a mildew condition, is the use of a first volume of a carrier paint. A second volume of an herbal mixture is then mixed into the first volume of carrier paint. The second volume comprises between about 8 and 16 drops of *Pinus sylvestris*, between about 8 and 16 drops of Thyme sweet, between about 8 and 16 drops of *Lavandula officinalis*, between about 8 and 16 drops of Lemon balm, and between about 8 and 16 drops of Eucalyptus. The second volume also has added into it between about 2 and 8 tablespoons of olive oil, between about 1 and 8 tablespoons of an alcohol, the preferred embodiment utilizing ethyl alcohol, between about ½ and 3 tablespoons of natural honey, and between about 1 and 5 deciliters of milk fat. The paint mixture being formulated for application to the surface in a room having a mildew condition therein.

As to the manner of usage and operation of the present invention, the same should be apparent from the above description. Accordingly, no further discussion relating to the manner of usage and operation will be provided.

With respect to the above description then, it is to be realized that the optimum relationships for the components of the invention, are deemed readily apparent and obvious to one skilled in the art, and all equivalent relationships described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact formulation as described, and accordingly, all suitable modifications and equivalents may be resorted to, falling within the scope of the invention.

What is claimed as being new and desired to be protected by Letters Patent of the United States is as follows:

1. An herbal paint mixture comprising, in combination:
   a carrier paint having a first volume;
   an herbal mixture having a second volume;
   the first volume of paint and the second volume of herbal mixture being mixed together, the first volume being ten liters;
   the herbal mixture second volume comprising a combination of herbal extracts mixed with a volume of Ethyl alcohol and volume of natural honey, the second volume comprising;
   5 drops of *Citrus medica* var. *Limonum*, and
   10 drops of *Cynnamomum ceylonicum*, and
   10 drops of *Pogostemon patchouli*, and
   10 drops of *Rosmarinus officinalis*, and 10 drops of *Eugenia coryophyllata*, and
5 drops of *Pimpinella anisum*;
the second volume also comprising;
5 tablespoons of Olive Oil; and
the Ethyl alcohol volume being 3 tablespoons; and
the natural honey volume being 1 tablespoon; and
3 deciliters of Milk Fat;
the carrier paint having a color added thereto and having a consistency for allowing the paint to be applied to and adherent to a surface; and
the mixture being applied as a paint to a surface, with the paint being allowed to dry.

2. The herbal paint mixture as described in claim 1 with the mixture further comprising the carrier paint being a water soluable paint.

3. The herbal paint mixture as described in claim 1 with the mixture further comprising the carrier paint being an oil based paint.

4. The herbal paint mixture as described in claim 1 with the mixture further comprising:
the carrier paint having a color added thereto and having a consistency for allowing the paint to be applied to and adherent to a surface in a fitness room.

5. The herbal paint mixture as described in claim 4 with the mixture further comprising the carrier paint being a water soluable paint.

6. The herbal paint mixture as described in claim 4 with the mixture further comprising the carrier paint being an oil based paint.

7. An herbal paint mixture comprising in combination:
a carrier paint having a first volume, the first volume being ten liters;
an herbal mixture having a second volume;
the first volume and the second volume being mixed together;
the carrier paint having a color added thereto and having a consistency for allowing the paint to be applied to and adherent to a surface;
the second volume comprising;
15 drops of *Citrus sinensis*, and
15 drops of *Citrus nobilis*, and
5 drops of *Lavandula officinalis*, and
5 drops of *Pinus sylvestris*;
the second volume also comprising;
5 tablespoons of Olive Oil; and
the Ethyl alcohol volume being 3 tablespoons; and
the natural honey volume being 1 tablespoon; and
3 deciliters of Milk Fat;
the paint mixture being formulated for application to the surface in a child's room.

8. The herbal paint mixture as described in claim 7 with the mixture further comprising the carrier paint being a water soluable paint.

9. The herbal paint mixture as described in claim 7 with the mixture further comprising the carrier paint being an oil based paint.

10. An herbal paint mixture comprising in combination:
a carrier paint having a first volume with the first volume being ten liters, the carrier paint also having a color added thereto and having a consistency for allowing the paint to be applied to and adherent to a surface;
a second volume being mixed with the first volume, the second volume comprising;
10 drops of *Aniba roseadora*, and
10 drops of *Lsevendula off*, and
10 drops of *Citrus medica* var. *limonum*, and
8 drops of *Camnphora officinarum*; and
4 drops *Citrus sinensis*, and
8 drops of *Oscimum basilicum*;
the second volume also comprising;
5 tablespoons of Olive Oil; and
the Ethyl alcohol volume being 3 tablespoons; and
the natural honey volume being 1 tablespoon; and
3 deciliters of Milk Fat;
the paint mixture being formulated for application to the surface in a bedroom.

11. The herbal paint mixture as described in claim 10 with the mixture further comprising the carrier paint being a water soluable paint.

12. The herbal paint mixture as described in claim 10 with the mixture further comprising the carrier paint being an oil based paint.

13. An herbal paint mixture comprising in combination:
a carrier paint having a first volume with the first volume being ten liters, the carrier paint also having a color added thereto and having a consistency for allowing the paint to be applied to and adherent to a surface;
a second volume mixed with the first volume, the second volume comprising;
10 drops of *Citrus sinesis*, and
15 drops of *Thymus vulgaris*, and
5 drops of *Eucalyptus globules*, and
5 drops of *Oscimum basilicum*, and
15 drops of *Citrus aurantium*, and
10 drops of *Pinus sylvestris*;
the second volume also comprising;
5 tablespoons of Olive Oil; and
the Ethyl alcohol volume being 3 tablespoons; and
the natural honey volume being 1 tablespoon; and
3 deciliters of Milk Fat;
the paint mixture being formulated for application to the surface in a workroom.

14. The herbal paint mixture as described in claim 13 with the mixture further comprising the carrier paint being a water soluable paint.

15. The herbal paint mixture as described in claim 13 with the mixture further comprising the carrier paint being an oil based paint.

16. An herbal paint mixture comprising in combination:
a carrier paint having a first volume with the first volume being ten liters, the carrier paint also having a color added thereto and having a consistency for allowing the paint to be applied to and adherent to a surface;
a second volume mixed with the first volume, the second volume comprising;
12 drops of *Pinus sylvestris*, and
12 drops of Thyme sweet, and
12 drops of *Lavandula officinalis*, and
12 drops of Lemon balm, and
12 drops of Eucalyptus;
the second volume also comprising;
5 tablespoons of Olive Oil; and
the Ethyl alcohol volume being 3 tablespoons; and
the natural honey volume being 1 tablespoon; and
3 deciliters of Milk Fat;
the paint mixture being formulated for application to the surface in a room having a mildew condition.

17. The herbal paint mixture as described in claim 16 with the mixture further comprising the carrier paint being a water soluable paint.

18. The herbal paint mixture as described in claim 16 with the mixture further comprising the carrier paint being an oil based paint.

* * * * *